United States Patent
Friedrich et al.

(10) Patent No.: US 8,090,185 B2
(45) Date of Patent: Jan. 3, 2012

(54) METHOD FOR OPTICAL INSPECTION, DETECTION AND VISUALIZATION OF DEFECTS ON DISK-SHAPED OBJECTS

(75) Inventors: Ralf Friedrich, Giessen (DE); Daniel Skiera, Langgoens (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 497 days.

(21) Appl. No.: 12/316,601

(22) Filed: Dec. 15, 2008

(65) Prior Publication Data

US 2009/0161097 A1    Jun. 25, 2009

(30) Foreign Application Priority Data

Dec. 19, 2007    (DE) .......................... 10 2007 047 928
Jan. 18, 2008    (DE) .......................... 10 2008 002 753

(51) Int. Cl.
*G06K 9/36*    (2006.01)
*G01N 21/88*    (2006.01)

(52) U.S. Cl. ...... 382/141; 382/145; 382/149; 356/237.5

(58) Field of Classification Search .................. 382/141, 382/145, 147, 149–152; 356/237.1–237.5
See application file for complete search history.

(56) References Cited

U.S. PATENT DOCUMENTS

| 5,859,698 | A | 1/1999 | Chau et al. ..................... 356/237 |
| 6,182,512 | B1 * | 2/2001 | Lorraine ......................... 73/655 |
| 6,559,457 | B1 * | 5/2003 | Phan et al. ................. 250/491.1 |
| 6,603,540 | B1 | 8/2003 | Kaupp ......................... 356/237.1 |
| 7,193,699 | B2 * | 3/2007 | Michelsson ................ 356/237.5 |
| 7,295,695 | B1 * | 11/2007 | Dayal ............................ 382/145 |
| 7,375,830 | B2 * | 5/2008 | Angellier ..................... 356/630 |
| 7,433,031 | B2 * | 10/2008 | Xu et al. ..................... 356/237.2 |
| 7,657,077 | B2 * | 2/2010 | Michelsson et al. .......... 382/144 |
| 7,738,692 | B2 * | 6/2010 | Chen et al. .................... 382/141 |
| 7,813,538 | B2 * | 10/2010 | Carroll et al. ................. 382/128 |
| 2007/0076194 | A1 | 4/2007 | Michelsson et al. ....... 356/237.1 |
| 2008/0062415 | A1 | 3/2008 | Michelsson ................ 356/237.2 |

FOREIGN PATENT DOCUMENTS

| DE | 199 04 427 | 9/2000 |
| DE | 103 07 358 | 10/2004 |
| DE | 10 2005 014 594 | 10/2006 |
| DE | 10 2006 042 956 | 10/2007 |
| JP | 04-123454 | 4/1992 |

* cited by examiner

*Primary Examiner* — Sang Nguyen

(74) *Attorney, Agent, or Firm* — Davidson, Davidson & Kappel, LLC

(57) ABSTRACT

A method for optical inspection, detection and visualization of defects (9) on wafers (2) is disclosed, wherein at least one camera (5) acquires images of at least one portion (11) of the wafer (2) relative to a reference point (12) of the wafer (2), and the Cartesian coordinates of the image data associated with the at least one portion (11) of the wafer (2) are transformed into polar coordinates.

20 Claims, 3 Drawing Sheets

METHOD FOR OPTICAL INSPECTION, DETECTION AND VISUALIZATION OF DEFECTS ON DISK-SHAPED OBJECTS

This claims the benefits of German Patent Application No. 10 2007 047 928.1, filed on Dec. 19, 2007, and German Patent Application No. 10 2008 002 753.7, filed on Jan. 18, 2008, both of which hereby incorporated by reference herein.

The invention relates to a method for optical inspection, detection and visualization of defects. In particular, the invention relates to a method for optical inspection, detection and visualization of defects, wherein at least one camera acquires images of at least one portion of the wafer relative to a reference point of the wafer.

BACKGROUND

Regarding the wafers used for wafer inspection, the resist is removed from the wafer edge in several processing steps by means of EBR (Edge Bead Removal). In this way, an edge bead removal line is generated. As a result, the wafer surface is stepped, which, in the acquired wafer image, can be seen as an ellipse or ideally as a concentric circle.

It is often difficult to find defects or anomalies on the wafer. Specifically, with respect to the edge area of the wafer, the EBRs of the edge area generally do not represent any defect for the user, but at the same time anomalies in this edge area should be detected. However, a problem in detecting such defects or anomalies in the edge area consists in distinguishing clearly between EBR and defect. Correspondingly, it is also often difficult to distinguish clearly between defects and desired structures on the wafer on the rest of the surface of the wafer.

Patent application DE 10 2005 014 594 discloses a method of detecting incomplete edge bead removal from a disk-like object, for example a wafer. For this purpose, first a peripheral area of a disk-like reference object is imaged. Marks are then defined in the peripheral area of the reference object. Finally, images of peripheral areas of a plurality of disk-like objects of the same batch are acquired. The inspection of the disk-like objects is limited to the locations of the marks defined on the reference object.

Patent application DE 10 2006 042 956 discloses a method of visualizing measured values from acquired images of disk-like objects. First an acquired image of at least one disk-like object is acquired, and a plurality of measured values is generated. A color value is assigned to each measured value. Finally, a resulting image is generated, wherein a color value selected from a predetermined range is assigned to an area that yielded a measured value on the disk-like substrate.

U.S. Pat. No. 5,859,698 discloses a method and an apparatus for macro-defect detection, wherein scattered light is used for image acquisition. The macro-defects may be located on a wafer, a partly processed wafer or on a liquid crystal display element. These defects are detected using scattered light. By means of an automated image processing technique, a reference image and a sample image are generated from the scattered light data. Then a difference image is generated by comparing the reference image and the sample image. The difference image is evaluated using at least one automated image processing technique, such as thresholding, morphological transformation and blob analysis, to identify macro-defects. However, only a transformation within the x-y coordinate system is performed instead of a polar coordinate transformation.

Japanese patent no. H04-123454 discloses a method for analyzing spurious particles or defects on a wafer. An interface is provided for converting the file and for the coordinate transformation of the spurious particle coordinate data to allow quick detection of spurious particles on the wafer. For this purpose, a wafer is inserted into a dust detector to detect the spurious particles. The x-y coordinates of the detected particles on the wafer are then stored in a storage medium. Then the wafer is removed from the detector and deposited on an automatic table of an inspection device. At the same time, the storage medium is removed from the detector and inserted into a computer connected to the inspection device to perform a coordinate transformation by converting the file containing the coordinate data. As soon as a spurious particle is identified, a control element is actuated to move the automatic x-y table such that the particle may be moved into the field of view and an image may be generated on the display. Again, only a transformation within the x-y coordinate system is performed instead of a polar coordinate transformation.

SUMMARY OF THE INVENTION

In the above prior art devices and methods, the acquired images of the wafer or of wafer portions are partially transformed, but the transformations are not specifically optimized for processing azimuthal and radial image contents separately.

It is an object of the present invention to provide a method for optical inspection, detection and visualization of defects during wafer inspection which detects and visually represents defects on the wafer in a simple and reliable way. In particular, the invention is to allow defect detection in image areas with high rotationally symmetric signal proportions.

The present invention provides a method for optical inspection, detection and visualization of defects during the inspection of a wafer, at least one camera acquiring images of at least one portion of the wafer. The portion may also encompass the whole wafer. A reference point is determined for the wafer, which serves as a reference point for the transformation to be performed. The Cartesian coordinates of the image data associated with the at least one portion of the wafer are to be transformed into polar coordinates. In one embodiment of the inventive method, the portion of the wafer whose Cartesian image coordinates are to be transformed into polar coordinates is given by the user, for example such that the user specifies an interval for the angle and an interval for the radius within which the portion of the wafer is situated. In one special embodiment, an area between 0° and 360° is given as the interval for the angle, and an area between r-ϵ and r is given as the interval for the radius, wherein r is the radius of the wafer or the maximum radius of the wafer if the wafer is not completely circular, and ϵ is a distance larger than zero to the wafer edge. In this embodiment, the portion of the wafer to be transformed thus includes the whole edge area of the wafer. If the angle is chosen to be less than 360 degrees, the portion of the wafer to be transformed is only a part of the edge area.

In one embodiment, several cameras may be used, whose single-line images are combined by a program to form a whole image. A similar arrangement is known from wafer backside inspection. Here, several cameras are, for example, used for image acquisition. Then the portion is extracted from the whole image. In another possible embodiment, only one camera is used, which captures the single lines one after the other. A program combines the single lines to form a whole image. The whole image or a partial image of the wafer may also be acquired by a meander scan.

The portion of the wafer may also be a sector of a circle, an annulus or part of an annulus, which are also converted to a rectangle by polar coordinate transformation.

If the portion of the wafer is a segment of a circle, the polar coordinate transformation yields a triangular strip or a rectangle.

In a further embodiment of the invention, the azimuthal and/or radial image contents are extracted or suppressed in the further image processing by anisotropic filtering after the polar coordinate transformation. Various prior art methods may be used for this purpose: linear filters, Fourier transformation, wavelet transformation, recursive filtering of the partial polar coordinate image, for example by an infinite impulse response filter. The method of anisotropic mode subtraction is part of the invention. However, the invention is not intended to be limited to these methods, and instead applies to all methods used for extracting or suppressing azimuthal and/or radial image contents by anisotropic filtering.

In a further embodiment of the inventive method, defect images used for the further analysis of the defects are generated from the azimuthal and/or radial contents of the images acquired with the at least one camera by means of prior art thresholding.

BRIEF DESCRIPTION OF THE DRAWINGS

In the following, the inventive method will be explained in more detail with reference to the schematic drawings, in which.

DETAILED DESCRIPTION

Figure 1:
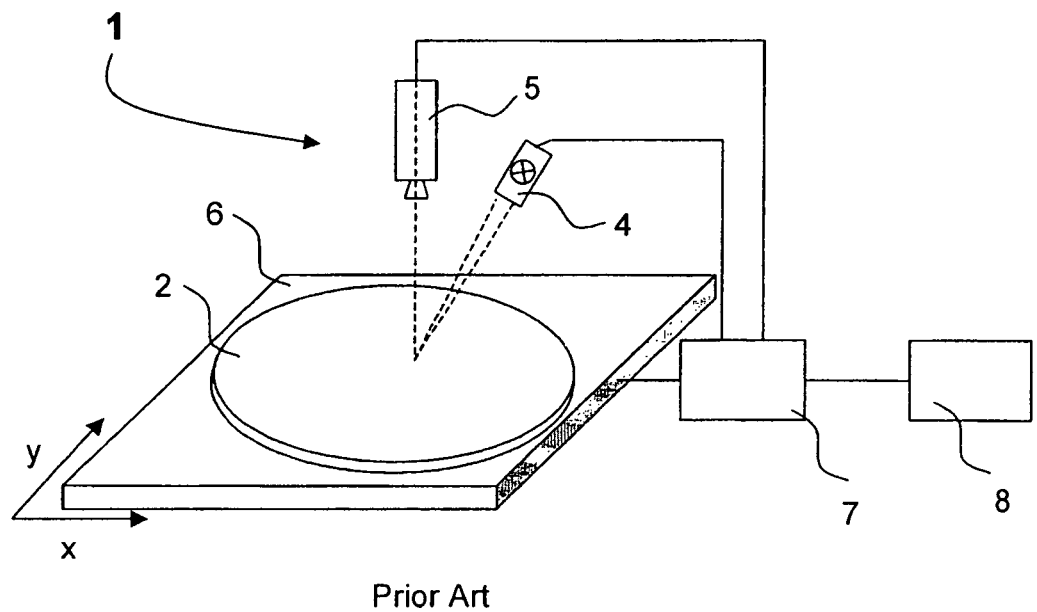
FIG. 1 shows a schematic representation of a device for acquiring an image.

FIG. 1 schematically shows a prior art device 1 for processing the image data of the surface of a wafer 2 acquired by a camera 5. The wafer 2 is situated on a scanning table 6. A plurality of images of the wafer 2 is acquired by the camera 5. In order to generate a relative movement between the scanning table 6 and the camera 5, an x-y scanning table is used in this embodiment, which may be moved in the x-coordinate direction and/or y-coordinate direction, wherein the x and y coordinate axes form a Cartesian coordinate system. The camera 5 is fixedly installed opposite the scanning table 6. It is obvious that, conversely, the scanning table 6 may also be fixedly installed and the camera 5 may be moved across the wafer 2 for image acquisition. A combination of the movement of the camera 5 in one direction and the scanning table 6 in the direction perpendicular thereto is also possible.

The wafer 2 is illuminated by an illumination means or illuminator 4 illuminating at least areas on the wafer 2 that essentially correspond to the field of view of the camera 5. Due to the concentrated illumination, which may additionally also be pulsed by means of a flash lamp, image acquisition on the fly is possible, wherein the scanning table 6 or the camera 5 are moved without stopping for the image acquisition. This allows a high wafer throughput. It is obvious that the relative movement between the scanning table 6 and the camera 5 may also be stopped for each image acquisition, and the wafer 2 may also be illuminated on its entire surface. The scanning table 6, the camera 5 and the illumination means 4 are controlled by a control unit 7. The acquired images may be stored in a computer 8 and may also be processed therein, if necessary.

Figure 2:
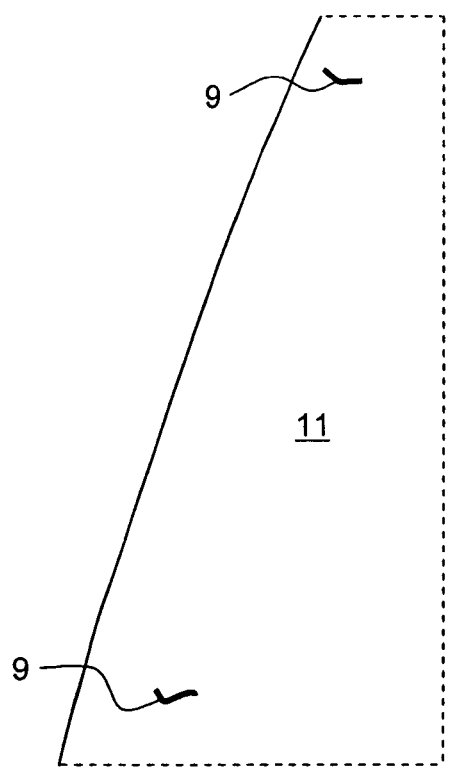
FIG. 2 shows an image of a portion of a wafer with two schematically illustrated defects.

FIG. 2 shows the image of a portion 11 of a wafer 2 with two schematically illustrated defects 9, acquired by a camera 5. The image of the portion 11 is transformed into polar coordinates and then yields the image 17 of FIG. 5.

Figure 3:
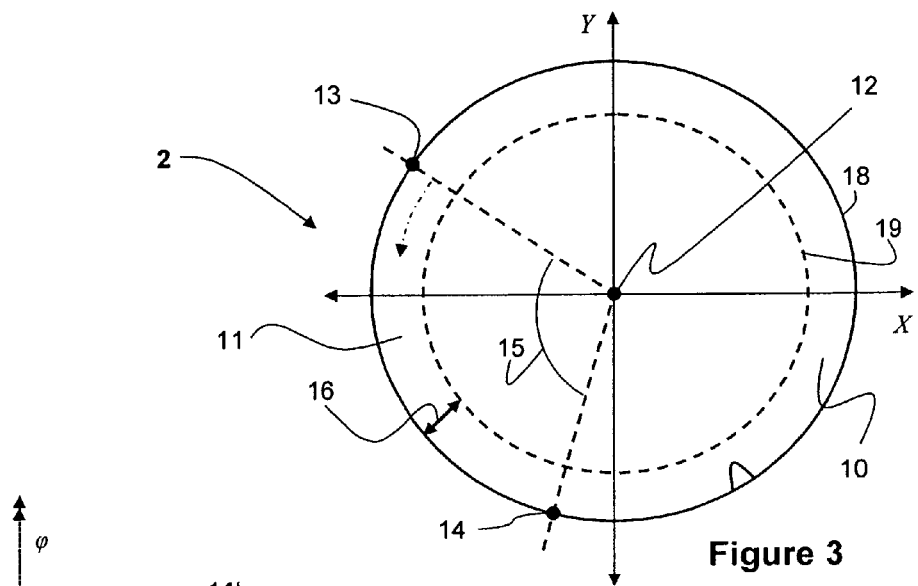
FIG. 3 shows a schematic top view of a wafer.

FIG. 3 shows a schematic top view of a wafer 2. The edge area 10 of the wafer 2 is bounded by the outer edge 18 of the wafer 2 and the broken inner circular line 19.

The Cartesian coordinate system is given by the reference point 12 and the X-axis and the Y-axis. In the embodiment of the invention shown in FIG. 3, the reference point 12 is the center of the wafer 2 (COW; center of wafer) and simultaneously the origin of the Cartesian coordinate system, which, however, is not to be considered as limiting the invention, because the reference point 12 may also be situated anywhere other than the center of the wafer 2.

The portion 11, which is converted to polar coordinates in the embodiment of FIG. 3, is part of the edge area 10. Although the following description of the invention relates only to the edge area 10 or part of the edge area 10, this is not to be considered as limiting the invention. It is obvious for someone skilled in the art that the present invention may be applied to any portion 11 or the entire surface of the wafer 2.

In the embodiment shown in FIG. 3, the portion 11 given for the polar coordinate transformation is defined by a starting point 13, an end point 14 for the given angle interval 15 of the portion 11 and by a radius interval 16. In the embodiment shown in FIG. 3, the starting point 13 and the end point 14 are both located on the outer boundary of the wafer 2, which, however, is not to be considered as limiting the invention, because the starting point 13 and the end point 14 may be located anywhere on the wafer 2 to define the portion 11 to be transformed. If the portion 11 has an irregular shape, correspondingly more points and/or lines must be specified to define the portion 11.

In the present embodiment of FIG. 3, the angle at the starting point 13 is 0 degrees. At the end point 14, the angle is larger than 0 degrees and may be up to 360 degrees.

Figure 4:
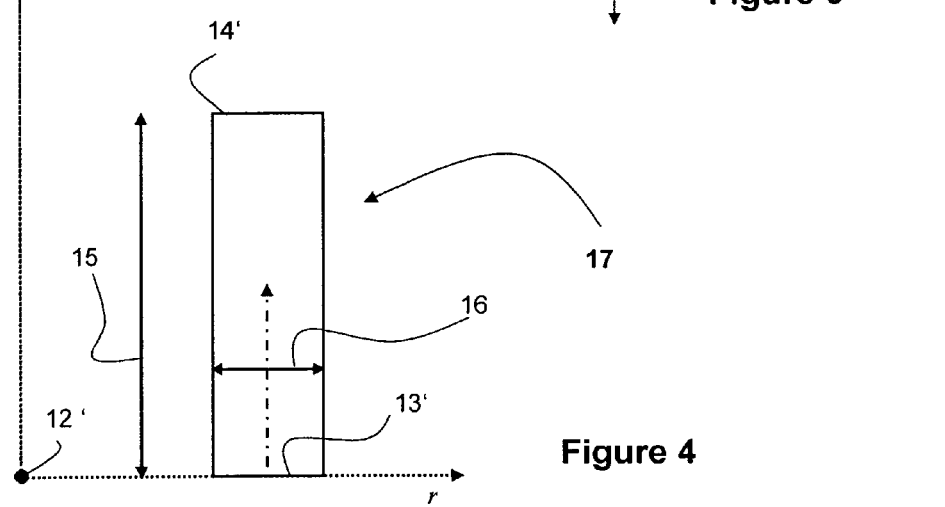
FIG. 4 shows a diagram of a transformed image of the portion of the wafer.
Figure 5:
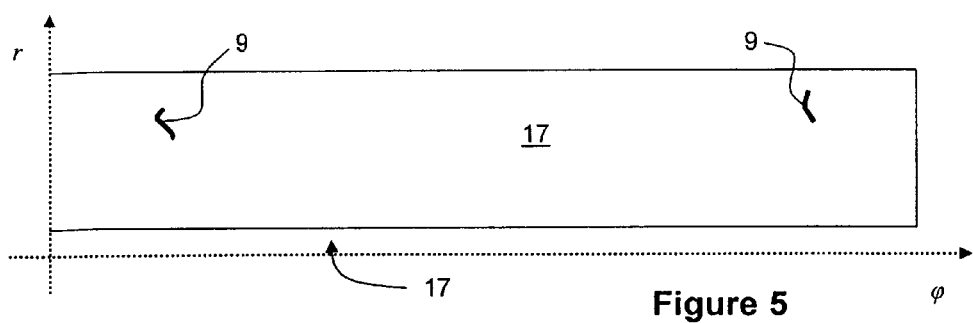
FIG. 5 shows the transformed image of the portion of the wafer of FIG. 2.

FIG. 4 shows a diagram of the image 17 of the portion 11 of the wafer 2 of FIG. 3, which is transformed into polar coordinates (see also FIG. 5). The polar coordinate system is formed by the r-axis for the radius and the φ-axis for the angle. The reference point 12 is transformed into the transformed reference point 12'.

The height of the image 17 represents the angle interval 15, the width of the image 17 represents the radius interval 16. The circle section-like portion 11 shown in FIG. 3 is transformed into a rectangular image 17 according to FIG. 4 by polar coordinate transformation.

FIG. 5 shows the transformed image 17 of the portion 11 of the wafer 2 of FIG. 2. Here, the coordinates associated with the two defects 9 are polar coordinates. If data points are missing in the portion 11 of FIG. 2 so that polar coordinate transformation of the acquired portion 11 does not yield a complete rectangle, these data points may be added for the portion 11 by the program performing the polar coordinate transformation.

The advantage of the invention is particularly obvious if, as shown in FIG. 3, portions 11 have a constant radius interval 16 for the entire angle interval 15, i.e. the portion 11 encompasses the same radius interval 16 for every angle of the angle interval 15. In these cases, an image 17 in the shape of a rectangle results from the polar coordinate transformation, as described above. Simple filterings, which then yield defect images, may be applied to such a rectangular image 17 according to the methods described above. In these defect images resulting from the filtering, defects 9 may be detected more easily and reliably as compared to the image of the portion 11 of the circular wafer 2. The invention is thus particularly suitable for cameras 5 designed as line cameras. As described above, the length of the camera line determines the radius interval 16 of the portion 11. Since the length of the camera line is always the same and line cameras normally move in a circular manner relative to the wafer 2, the radius interval 16 of the portion 11 is also constant for the entire angle interval 15, and the transformed image 17 is a rectangle.

Portions 11 having other shapes are transformed into other shapes of an image 17, as is well known from the theory regarding transformation functions.

Figure 6:
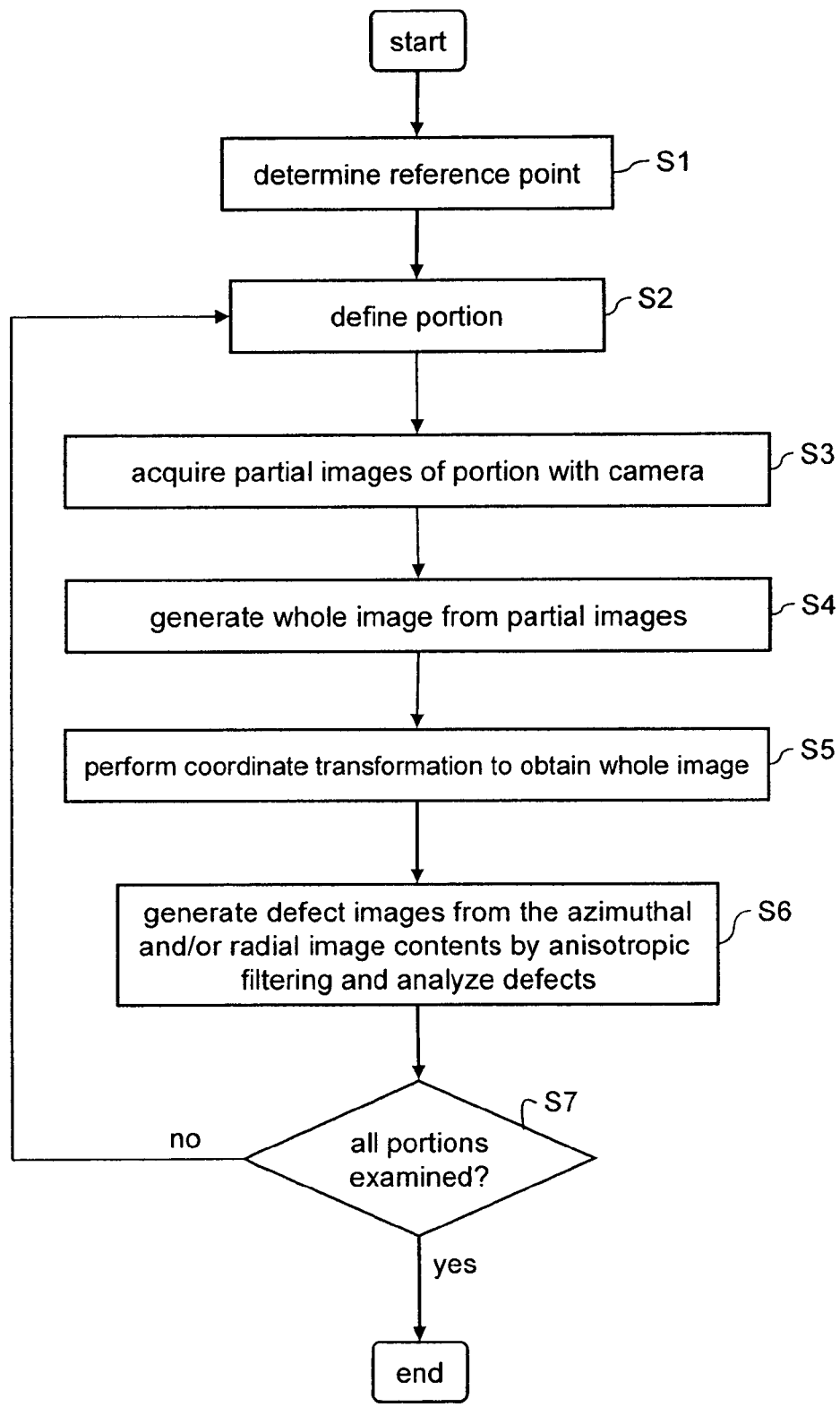
FIG. 6 shows a flowchart associated with an embodiment of the inventive method.

FIG. 6 shows a flowchart associated with an embodiment of the inventive method. In a first step S1, the Cartesian coordinate system and a reference point 12 are defined. The images to be acquired are related to a Cartesian coordinate system and the reference point 12. In a second step S2, a portion 11 of the wafer 2 to be inspected for defects 9 is defined as described above, preferably with a constant radius interval 16 for the whole angle interval 15, such as it is the case in the inspection of the edge area 10 of the wafer 2 as portion 11 with the help of a line camera. In a third step S3, a plurality of partial images of the portion 11 of the wafer 2 are acquired one after the other with the at least one camera 5. The entire portion 11 may also be captured in a single image, depending on the type of camera 5 and the definition of the portion 11. If, for example, the camera 5 is a line camera, and the portion 11 is the edge area 10, the line-shaped partial images of the edge area 10 are acquired line by line.

In a fourth step S4, a complete image of the portion 11 of the wafer 2 is generated from the acquired partial images. In the example of the line camera and the edge area 10 as portion 11, all line images combined form a complete image of the captured edge area 10 of the wafer 2.

In a fifth step S5, the complete image of the portion 11 is transformed into polar coordinates resulting in a complete image 17 in polar coordinate representation, preferably in the shape of a rectangle, as described above.

In a sixth step S6 of the embodiment, various further defect images may be generated from the azimuthal and/or radial image contents for a better and more reliable analysis of potential defects 9. The defect images may be generated by anisotropic filtering according to one of the methods described above. In anisotropic mode subtraction, the mode of the pixel values from a freely definable rectangular environment is subtracted from the value of each pixel.

According to the query in the seventh step S7, when the current portion 11 has been processed, a next portion 11 of the wafer 2 may be examined according to the steps described above, until all portions 11 of the wafer 2 have been processed.

Finally, it should be noted in particular, that the previously described exemplary embodiments, only serve to describe the teachings claimed, and are not limiting to the exemplary embodiments. It is conceivable however for someone skilled in the art, that variations and modifications of the invention can be made without departing from the scope of protection of the appended claims.

What is claimed is:

1. A method for optical inspection, detection and visualization of defects on wafers comprising:
    acquiring, using at least one camera, images of at least one portion of the wafer relative to a reference point of the wafer;
    transforming, using a computer, Cartesian coordinates of the image data associated with the at least one portion of the wafer into polar coordinates; and
    extracting or suppressing, using a computer, at least one of azimuthal and radial image contents by anisotropic filtering after the polar coordinate transformation.

2. The method as recited in claim 1 further comprising predetermining by a user the portion of the wafer whose Cartesian image coordinates are to be transformed into polar coordinates.

3. The method as recited in claim 2 wherein the user predetermines an interval for the angle and an interval for the radius, within which the portion of the wafer whose Cartesian image coordinates are to be transformed into polar coordinates is located.

4. The method as recited in claim 1 wherein the portion of the wafer is the entire wafer.

5. The method as recited in claim 1 wherein the portion of the wafer is the entire edge area.

6. The method as recited in claim 1 wherein the portion of the wafer is a part of the edge area.

7. The method as recited in claim 1 wherein the portion of the wafer is a sector.

8. The method as recited in claim 1 wherein the portion of the wafer is a segment.

9. The method as recited in claim 1 wherein the portion of the wafer is an annulus or a part of an annulus.

10. The method as recited in claim 1 wherein an anisotropic mode subtraction is used for the anisotropic filtering.

11. The method as recited in claim 1 wherein linear filters are used for the anisotropic filtering.

12. The method as recited in claim 1 wherein a Fourier transformation is used for the anisotropic filtering.

13. The method as recited in claim 1 wherein a wavelet transformation is used for the anisotropic filtering.

14. The method as recited in claim 1 wherein recursive filtering of the partial polar coordinate image is used for the anisotropic filtering.

15. The method as recited in claim 1 wherein an anisotropic mode subtraction is applied to an image or a partial image.

16. The method as recited in claim 1 further comprising generating defect images from at least one of azimuthal and radial contents of the images acquired with the at least one camera using thresholding.

17. The method as recited in claim 1 wherein the camera is a line camera.

18. The method as recited in claim 1 wherein the at least one portion of the wafer is a first shape and the transformation converts an image of the first shape into an image of a second shape.

19. The method as recited in claim 18 wherein the first shape is an annulus or part of an annulus and the second shape is a rectangle.

20. The method as recited in claim 18 wherein the first shape is a segment of a circle and the second shape is a triangular strip or a rectangle.

* * * * *